United States Patent
Clayton

(10) Patent No.: US 7,436,932 B2
(45) Date of Patent: Oct. 14, 2008

(54) X-RAY RADIATION SOURCES WITH LOW NEUTRON EMISSIONS FOR RADIATION SCANNING

(75) Inventor: James E. Clayton, Henderson, NV (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 0 days.

(21) Appl. No.: 11/165,972

(22) Filed: Jun. 24, 2005

(65) Prior Publication Data
US 2006/0291628 A1    Dec. 28, 2006

(51) Int. Cl.
H01J 35/08 (2006.01)

(52) U.S. Cl. ................................ 378/143; 378/119

(58) Field of Classification Search ............ 378/119, 378/121, 122, 142, 143, 144; 313/363.1, 313/359.1, 231.01–231.71; 250/505.1, 515.1
See application file for complete search history.

(56) References Cited

U.S. PATENT DOCUMENTS

| | | | | |
|---|---|---|---|---|
| 4,317,035 | A * | 2/1982 | Cohen et al. | 378/47 |
| 5,115,459 | A * | 5/1992 | Bertozzi | 378/88 |
| 5,124,658 | A | 6/1992 | Adler | |
| 5,874,811 | A | 2/1999 | Finlan et al. | |
| 6,009,146 | A | 12/1999 | Adler et al. | |
| 6,069,936 | A | 5/2000 | Bjorkholm | |
| 6,172,463 | B1 | 1/2001 | Cutler et al. | |
| 6,445,766 | B1 | 9/2002 | Whitham | |
| 6,463,123 | B1 * | 10/2002 | Korenev | 378/69 |
| 6,493,424 | B2 * | 12/2002 | Whitham | 378/137 |
| 6,628,745 | B1 | 9/2003 | Annis et al. | |
| 6,683,318 | B1 * | 1/2004 | Haberer et al. | 250/492.3 |
| 2005/0077472 | A1 * | 4/2005 | Korenev | 250/360.1 |
| 2005/0218348 | A1 * | 10/2005 | Fehrenbacher et al. | 250/517.1 |
| 2005/0281383 | A1 * | 12/2005 | Harding et al. | 378/149 |

OTHER PUBLICATIONS

"Neutron Contamination From Medical Electron Accelerators", National Council on Radiation Protection and Measurements, NCRP Report No. 79, 1984, pp. i-vi and 1-60.
McCall, R. C., et al., "Neutron Sources and Their Characteristics", NBS SP, 1979, vol. 554, pp. 75-86, from Heaton, et al., ed., "Proceedings of a Conference on Neutrons from Electron Medical Accelerators", Proceedings of a Conference held at the National Bureau of Standards, Gaithersburg, MD, Apr. 9-10, 1979.
McCall, Richard C., et al., "Improvement of linear accelerator depth-dose curves", Med. Phys., Nov./Dec. 1978, vol. 5, No. 6, pp. 518-524.
Gozani, Tsahi, "Active Nondestructive Assay of Nuclear Materials: Principles and Applications", United States Nuclear Regulatory Commission, Jan. 1981, pp. 173-205.

(Continued)

Primary Examiner—Jurie Yun
(74) Attorney, Agent, or Firm—Brandon N. Sklar; Kaye Scholer LLP

(57) ABSTRACT

In one example, a radiation source comprises a housing and an acceleration chamber within the housing, with a peak acceleration energy greater than the lowest neutron production threshold of tantalum. A source of charged particles is supported by the housing to emit charged particles into the acceleration chamber. A target is supported by the housing downstream of the acceleration chamber. The target consists essentially of at least one isotope having a neutron production threshold greater than the peak acceleration energy. No neutrons are therefore generated. The source may also comprise a collimator, target shielding, and/or housing shielding comprising at least one isotope having a neutron production threshold greater than the peak acceleration energy, reducing or eliminating neutron generation as compared to the prior art, as well. Systems comprising the source, methods of operation of the source, and methods of manufacture of the source are also disclosed.

64 Claims, 8 Drawing Sheets

OTHER PUBLICATIONS

MatWeb, Oxygen-free electronic Copper, UNS C10100, http://www.matweb.com/search/SpecificMaterial.asp?bassnum=MC101A, at least as early as Dec. 28, 2004.

MatWeb, "GlidCop® AL-60 Dispersion Strengthened Copper", http://www.matweb.com/search/SpecificMaterial.asp?bassnum=NOMG60, at least as early as Dec. 28, 2004.

* cited by examiner

X-RAY RADIATION SOURCES WITH LOW NEUTRON EMISSIONS FOR RADIATION SCANNING

FIELD OF THE INVENTION

X-ray radiation sources and, more particularly, X-ray radiation sources with low neutron emissions for radiation scanning of objects.

BACKGROUND OF THE INVENTION

X-ray radiation sources are commonly used in radiation inspection systems for non-destructive inspection of objects. X-ray radiation may be generated in such sources by the impact of a beam of accelerated electrons on a high atomic number ("Z") target material, such as tungsten or tantalum. The electrons are accelerated by a potential difference established across a chamber, referred to as an acceleration energy. The deceleration of the incident electrons by the nuclei of the atoms of the target material generates radiation, referred to as Bremsstrahlung. A collimator is provided to direct some of the generated radiation onto an object to be inspected and to form the generated radiation into a beam of a desired size and shape. One or more radiation detectors are provided to measure radiation transmitted through and/or scattered from the object. The body of the radiation source may also be shielded. In order to prevent radiation from escaping the radiation inspection system, shielding is also provided around the system as a whole.

Small objects, such as luggage and carry-on bags, are typically examined by radiation in the kilovolt range. However, radiation in the kilovolt range may not penetrate objects thicker than about 5 feet (1.52 meters), particularly if the object is filled with dense material. Standard cargo containers are typically 20-50 feet long (6.1-15.2 meters), 8 feet high (2.4 meters) and 6-9 feet wide (1.8-2.7 meters). Air cargo containers, which are used to contain a plurality of pieces of luggage or other cargo to be stored in the body of an airplane, may range in size (length, height, width (thickness)) from about 35×21×21 inches (0.89×0.53×0.53 meters) up to about 240×118×96 inches (6.1×3.0×2.4 meters). Large collections of objects, such as many pieces of luggage, may also be supported on a pallet. Pallets, which may have supporting sidewalls, may be of comparable sizes as cargo containers, at least when supporting objects. The term "cargo conveyance" is used to refer to all types of cargo containers and comparably sized pallets (and other such platforms) supporting objects.

Higher energy radiation beams are required to penetrate through denser materials than less dense materials and through thicker materials than less thick materials. The low energies used in typical X-ray luggage and bag scanners, described above, are generally too low to penetrate through the much larger cargo containers, particularly those with widths or thicknesses of 5 feet (1.5 meters) or more. While the required energy level depends on the contents of the container and the width of the container, radiation in the megavolt range is typically required. 6 MeV to 10 MeV may be used, for example. 9 MeV is commonly used because it will penetrate through most cargo containers, regardless of the contents. However, high Z and medium Z metals commonly used in X-ray radiation sources, such as tungsten, tantalum, and molybdenum comprise stable isotopes having neutron production thresholds (the energy required to remove a neutron from a nucleus of an atom of the isotope) in a range of about 6 MeV to about 10 MeV. For example, the calculated neutron production thresholds for the stable isotopes of tungsten range from 6.191 MeV to 8.415 MeV. The calculated neutron production threshold for the stable isotope of tantalum is 7.651 MeV. The calculated neutron production thresholds for the stable isotopes of molybdenum range from 7.369 MeV to 12.667 MeV. Since 6 MeV to 10 MeV is a common range to examine cargo conveyances, neutrons are typically produced.

Because of their ability to absorb larger amounts of photons than lower atomic number metals per unit volume, high Z metals, such as tungsten and lead, are also typically used to shield the target and collimate the radiation beam. The stable isotopes of lead have calculated neutron production thresholds of from 6.737 MeV to 8.394 MeV. If the generated X-ray radiation used to examine the objects has an energy above the neutron production threshold of the shielding material and collimator, neutrons will also be produced.

Since neutrons may be harmful to people proximate the scanning system, thicker shielding may be required to prevent the escape of neutrons from the scanning system or the room containing the scanning system. This may increase the size and cost of the system. Concrete walls are commonly used to shield a room containing a scanning system, preventing or decreasing the amount of neutrons and X-rays that may escape the room. If space or other requirements prevent the use of concrete walls, then a multi-layer wall may be used. For example, a thick wall of polyethylene or borated polyethylene may be used as an inner layer to shield neutrons and lead or steel may be used as an outer layer to shield X-rays. The outer layer also shields gamma rays emitted by the polyethylene.

Varian Medical Systems, Inc., ("Varian") Palo Alto, Calif., sells X-ray radiation sources for medical therapy supported by a rotatable gantry that also supports a detector array. The gantry, the source, and the detector comprise an integrated unit, which is sold under the trade name CLINAC®. The radiation source comprises a copper target and tungsten shielding. Copper generates sufficient X-ray radiation for therapeutic purposes, and is less expensive than tungsten. CLINACs® are available at 4 MeV, 6 MeV, 10 MeV and above. Copper has two stable isotopes, copper-65, with a calculated neutron production threshold of 9.910 MeV, and copper-63, with a calculated neutron production threshold of 10.852 MeV. Since in the 10 MeV and above models of the CLINAC® the acceleration energy is above the neutron production threshold of copper-65 and tungsten, neutrons are produced. The collimator comprises a combination of tungsten and lead, which will also generate neutrons. The tungsten shielding will generate neutrons, as well.

Efforts have been made to reduce neutron emission from X-ray sources used in medical therapy, such as radiation treatment. See, for example, Neutron Contamination from Medical Electron Accelerators, NRCP Report No. 79, National Council on Radiation Protection and Measurements, Bethesda, Md., pp. 59-60 (1995). It is said to be difficult to reduce the number of neutrons produced per useful photon rad of radiation, in the space available in existing sources. (Id.) It is noted that neutron emission may be reduced by absorbing unwanted neutrons in a medium Z material, such as iron, instead of tungsten or lead; but it is also noted that much more iron is required than tungsten or lead and there is insufficient space to take advantage of this reduction completely. (Id.)

Varian also sells a Linatron® series of X-ray sources that generate X-ray radiation in the range of 1-10 MeV. In these sources, the target is tungsten, typically in the form of a disk. A disk of copper is attached to the downstream side of the tungsten, of the electron beam, to dissipate heat and to act as a final electron stop for electrons passing through the tungsten target. The tungsten target is the primary source of X-ray radiation. It is believed that a small amount of X-ray radiation may be generated by the copper disk as well, by the electrons passing through the tungsten target. If the acceleration energy of the source is greater than the neutron production threshold of the tungsten, neutrons may be produced.

SUMMARY OF THE INVENTION

In accordance with one embodiment of the invention, a radiation source is disclosed comprising a housing and an acceleration chamber within the housing. The acceleration chamber has a peak acceleration energy greater than the neutron production threshold of tantalum, during use. A source of charged particles is supported by the housing to emit charged particles into the acceleration chamber. A target is supported by the housing downstream of the acceleration chamber. Impact of the target by the accelerated charged particles generates radiation. The target consists essentially of at least one isotope having a neutron production threshold greater than the peak acceleration energy. The peak acceleration energy may be greater than about 7.7 MeV, for example. In a source with a peak acceleration energy greater than the peak acceleration energy of tantalum, targets comprising tungsten, tantalum, or molybdenum, which include isotopes with neutron production thresholds less than the peak acceleration energy, neutrons are generated.

In one example, if the peak acceleration energy is less than or equal to 8 MeV, the target is chosen from the group consisting of at least one isotope of carbon, aluminum, scandium, titanium, vanadium, manganese, cobalt, and copper. In another example, if the peak acceleration energy is greater than 8 MeV and less than or equal to 9 MeV, the target is chosen from the group consisting of at least one isotope of aluminum, scandium, vanadium, manganese, cobalt, and copper. In another example, if the peak acceleration energy is greater than 9 MeV and less than or equal to 10 MeV, the target is chosen from the group consisting of at least one isotope of aluminum, scandium, manganese, and cobalt. In another example, if the peak acceleration energy is greater than 10 MeV and less than 11 MeV, the target is chosen from the group consisting of at least one isotope of scandium and aluminum. In another example, if the peak acceleration energy is greater than 11 and less than about 13.1 MeV, the target is aluminum. Copper is a preferred material if the peak acceleration energy is less than about 9.9 MeV.

The radiation source may further comprise a collimator, target shielding, and housing shielding. Any or all of these components may also comprise at least one isotope having a neutron production threshold greater than the peak acceleration energy.

In accordance with other embodiments of the invention, a radiation source is disclosed comprising a housing and an acceleration chamber within the housing. The acceleration chamber has a peak acceleration energy greater than the lowest neutron production threshold of tungsten, during use. A source of charged particles is supported by the housing to emit charged particles into the acceleration chamber. A target is supported by the housing downstream of the acceleration chamber. The peak acceleration energy may be greater than the lowest neutron production threshold of molybdenum or tantalum, as well. The peak acceleration energy may be greater than about 6.2 MeV, 6.8 MeV, or 7.7 MeV. In a collimator embodiment, a collimator is coupled to the housing, proximate the target material, and the collimator comprises at least one isotope having a neutron production threshold greater than the peak acceleration energy. In a target shielding embodiment, target shielding surrounds at least a portion of the target, and the target shielding comprises at least one isotope having a neutron production threshold greater than the peak acceleration energy.

It is noted that some of the advantages of the present invention may be obtained if only certain components of the source consist essentially of at least one isotope having a neutron production threshold greater than the peak acceleration energy of the source. Therefore, in the collimator embodiment, the collimator may comprise at least one first section consisting essentially of at least one isotope having a neutron production threshold greater than the peak acceleration energy and at least one second section comprising at least one isotope having a neutron production threshold less than the peak acceleration energy. In the target shielding embodiment, the target shielding may comprise at least one first section consisting essentially of at least one isotope having a neutron production threshold greater than the peak acceleration energy and at least one second section comprising at least one isotope having a neutron production threshold less than the peak acceleration energy. In either case, neutron production is reduced as compared to the use of prior art collimators and target shielding in radiation sources. The collimator and/or the target shielding may comprise copper.

In accordance with another embodiment, a radiation source is disclosed comprising a housing and an accelerator chamber within the housing. In this embodiment, the acceleration chamber has a peak acceleration energy of less than the lowest neutron production threshold of copper. A source of charged particles is supported by the housing to emit charged particles into the accelerator chamber and a target is supported by the housing, downstream of the accelerator chamber. A collimator is coupled to the housing proximate the target. Target shielding at least partially surrounds the target to shield the target. The target, the collimator, and the target shielding comprise copper. The peak acceleration energy may be less than about 9.9 MeV, for example. The peak acceleration energy may be less than or equal to about 9 MeV. The peak acceleration energy may be greater than the lowest neutron production threshold of tungsten, molybdenum, or tantalum, as well. The peak acceleration energy may be greater than about 6.1 MeV, 6.8 MeV, or 7.7 MeV.

The collimator may comprise a first section consisting essentially of copper, proximate the target, and a second section comprising at least one isotope having a neutron production threshold less than the peak acceleration energy, downstream of the first section. The target shielding may comprise a first section consisting essentially of copper, proximate the target and a second section comprising at least one isotope having a neutron production threshold less than the peak acceleration energy, upstream of the first section. The source may further comprise housing shielding to shield the housing, wherein the housing shielding comprises copper. Lead shielding may surround at least a portion of the collimator and the target shielding.

In accordance with another embodiment of the invention, a radiation source is disclosed, as above, wherein the target consists essentially of a low atomic number material comprising at least one isotope having a neutron production threshold greater than the peak acceleration energy of the source.

In accordance with another embodiment of the invention, a method of generating radiation is disclosed comprising accelerating charged particles to a peak acceleration energy greater than the lowest neutron production threshold of tantalum and colliding the charged particles with a target consisting essentially of at least one isotope having a neutron production threshold less than the peak acceleration energy. The method further comprises generating radiation from the collision of the charged particles with the target, without generating neutrons. The method may further comprise collimating the generated radiation by a collimator comprising at least one isotope having a neutron production threshold greater than the peak acceleration energy. The method may further comprise shielding the target with shielding material comprising at least one isotope having a neutron production threshold greater than the peak acceleration energy. The method may further comprise shielding the housing with shielding material comprising at least one isotope having a neutron production threshold greater than the peak acceleration energy. The peak acceleration energy may be greater than about 7.7 MeV, for example.

In accordance with another embodiment of the invention, a system for examining a cargo conveyance is disclosed comprising a radiation source positioned to irradiate an object and a detector to receive radiation after interacting with the object. The radiation source comprises a housing and an acceleration chamber supported by the housing. The acceleration chamber has a peak acceleration energy less than the lowest neutron production threshold of copper and greater than the lowest neutron production threshold of tungsten. The peak acceleration energy may be less than about 9.9 MeV, for example. The peak acceleration energy may be greater than 6.1 MeV, for example. A source of charged particles is supported by the housing to emit charged particles into the acceleration chamber and a target is supported by the housing downstream of the acceleration chamber. The target consists essentially of at least one isotope of copper. Other isotopes of other materials that will not generate neutrons at the peak acceleration energy of the source, may be included, without materially affecting the basic characteristics of the target with respect to neutron production. A collimator is coupled to the housing and target shielding is supported by the housing, partially around the target. Either or both of the collimator and the target shielding also comprises copper. The system may further comprise shielding material over at least a portion of the housing, which also comprises at least one isotope having a peak production threshold less than the peak acceleration energy. A conveyor adapted to support and convey a cargo conveyance may also be provided. The cargo conveyance may be greater than or equal to 5 feet thick. The cargo conveyance may be a standard cargo conveyance. The peak acceleration energy may be at least about 6.2 MeV. The peak acceleration energy may be at least about 7.7 MeV.

In accordance with another embodiment of the invention, a method of manufacturing a radiation source is disclosed comprising selecting for at least one of a target, a collimator, and target shielding (in other words, the target, the collimator, and/or the target shielding) at least one isotope having a neutron production threshold less than a peak acceleration energy of the source and assembling the source including the selected material. The method may further comprise selecting housing shielding material consisting essentially of at least one isotope having a neutron production threshold less than the peak acceleration energy and assembling the source with the selected housing shielding material.

The method may further comprise preparing a preliminary design for a radiation source to meet, at least, neutron production requirements, inputting the preliminary design into a simulation to predict neutron production, and receiving an output of the simulation. If the output does not meet requirements, the method may further comprise adjusting the design and inputting the adjusted design into the simulation to predict neutron production. The method may further comprise preparing the preliminary design based on size requirements and/or X-ray radiation generation requirements.

As used herein, the term "about" refers to differences due to round off errors and typical measurement capabilities; the term "at least one of" means "any one or more of the following"; the term "consisting essentially of" means that isotopes of the same and/or other materials that will not generate neutrons at the peak acceleration energy of the source, may be included; and the term "peak acceleration energy" means "maximum" acceleration energy.

DESCRIPTION OF THE PREFERRED EMBODIMENTS

In accordance with embodiments of the invention, radiation sources, such as X-ray radiation sources, provide no neutron production or reduced neutron production as compared to radiation sources comprising typical materials for the source, collimator, and/or shielding by using materials with neutron production thresholds above the peak acceleration energy of the source. (As mentioned above, here, the term "peak acceleration energy" means "maximum" acceleration energy.) For example, an X-ray source with a peak acceleration energy of less than about 9.9 MeV, comprising a copper target, a copper collimator, and copper shielding of the target and housing, will generate no neutrons. Where it is not feasible to use only materials with neutron production thresholds below the peak acceleration energy of the source due to size, weight, and/or cost constraints, neutron production may be reduced by using such materials for all or part of certain components. By proper selection of materials, no or reduced neutron production may be provided in radiation sources with peak acceleration energies, and hence peak radiation energies, in the range of from about 6.2 MeV to less than about 13.1 MeV.

One of the advantages of reduced or no neutron production is that the physical size of the shielding of the source and the scanning system as a whole, including the room containing the scanning system, may be reduced. Also, the risk of activation of certain materials of or within the object under test and the scanning room by neutron capture reactions, may also be reduced.

The class of materials that may be used is referred to herein as "low atomic number materials" or "low Z materials" because those materials have atomic numbers ("Z") significantly less than that of tungsten (Z=74), tantalum (Z=73), lead (Z=82), and molybdenum (42), the common materials used in the prior art. Copper, for example, has an atomic number of 29. In one example, the low Z material may have an atomic number Z of 30 or less. Appropriate low atomic number materials for a particular application have their lowest neutron production threshold greater than the peak acceleration energy of the source, so that no neutrons are generated by that material.

It has been found that due to their size differences, more neutrons may be generated by the shielding and collimator materials than by the target. It is also noted that not all low Z materials are appropriate in the preferred peak acceleration range for examining cargo conveyances of from about 6 MeV to 10 MeV, which is a useful range for examining cargo conveyances, which can be greater than 5 feet (1.524 meters) thick. Beryllium, for example, with an atomic number of 4, has the lowest neutron production threshold of all elements at 1.665 MeV.

Figure 1:
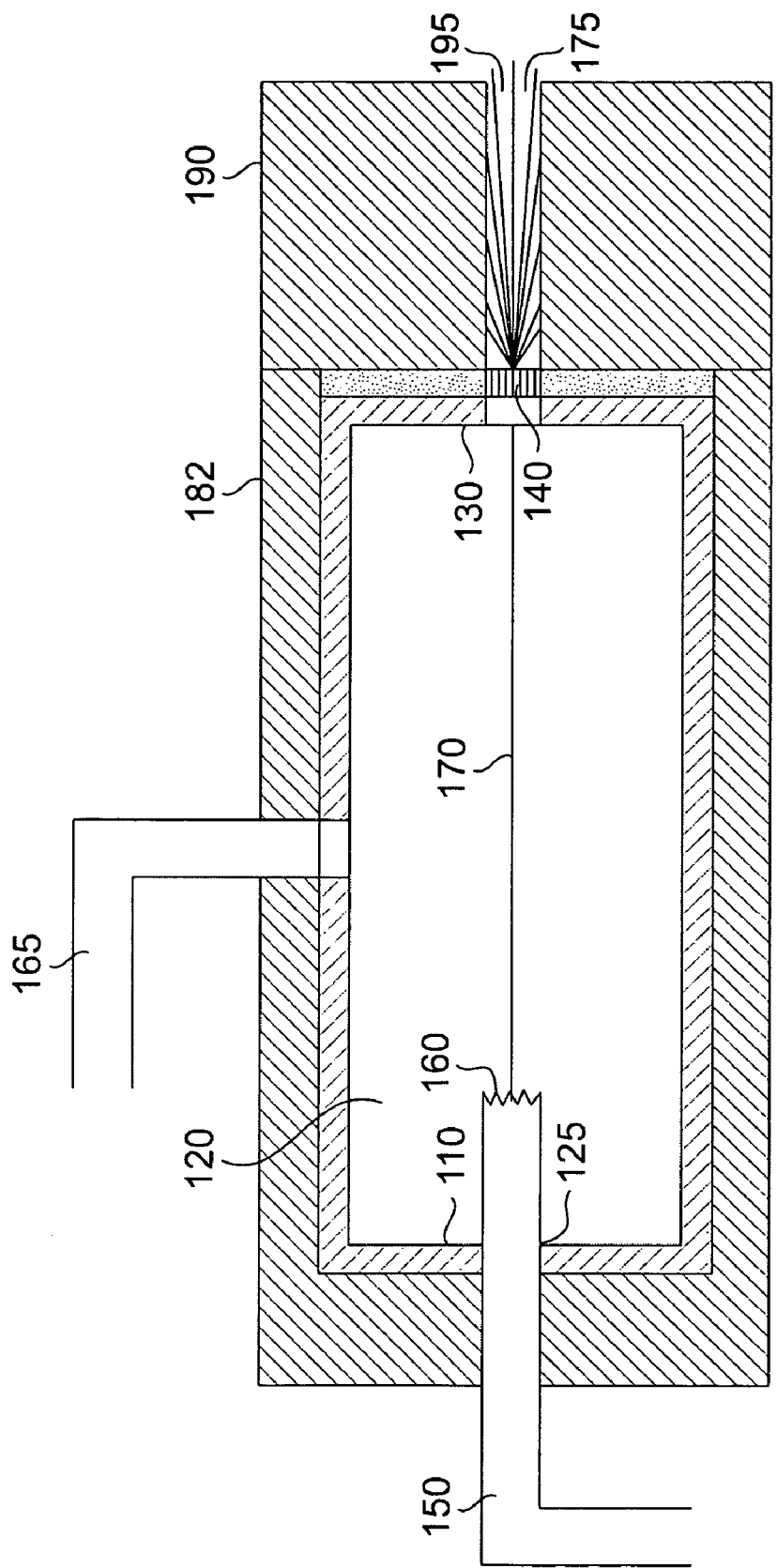
FIG. 1 is a schematic cross-sectional view of an example of a radiation source in accordance with an embodiment of the invention.

FIG. 1 is a schematic cross-sectional view of an example of a radiation source 100, such as an X-ray linear accelerator, in accordance with an embodiment of the present invention. The linear accelerator 100 comprises a housing 110 defining an acceleration chamber 120. The housing defines an input 125 and an output 130. A target 140 is supported in or near the output 130 of the housing 110. The target 140 is a material that generates Bremsstrahlung radiation in response to impact by accelerated charged particles. In one example, the target 140 preferably consists essentially of isotopes of a low Z material having a neutron production threshold less than the acceleration potential of the acceleration chamber 120. Copper may be used, for example. An electron gun 150 extends through the input 125. The electron gun comprises a filament 160, which is suspended in the acceleration chamber 120. A magnetron 165 is coupled to the acceleration chamber 120 to create an electromagnetic field within the acceleration chamber. The electromagnetic field accelerates electrons generated by the filament 160 to a desired energy level within the acceleration chamber 120. The accelerated electrons form an electron beam 170 that strikes the target 140 in the output 130, causing the emission of photons in the form of a beam of X-ray radiation 175. The housing 110 may comprise a thin copper wall, for example.

Figure 4:
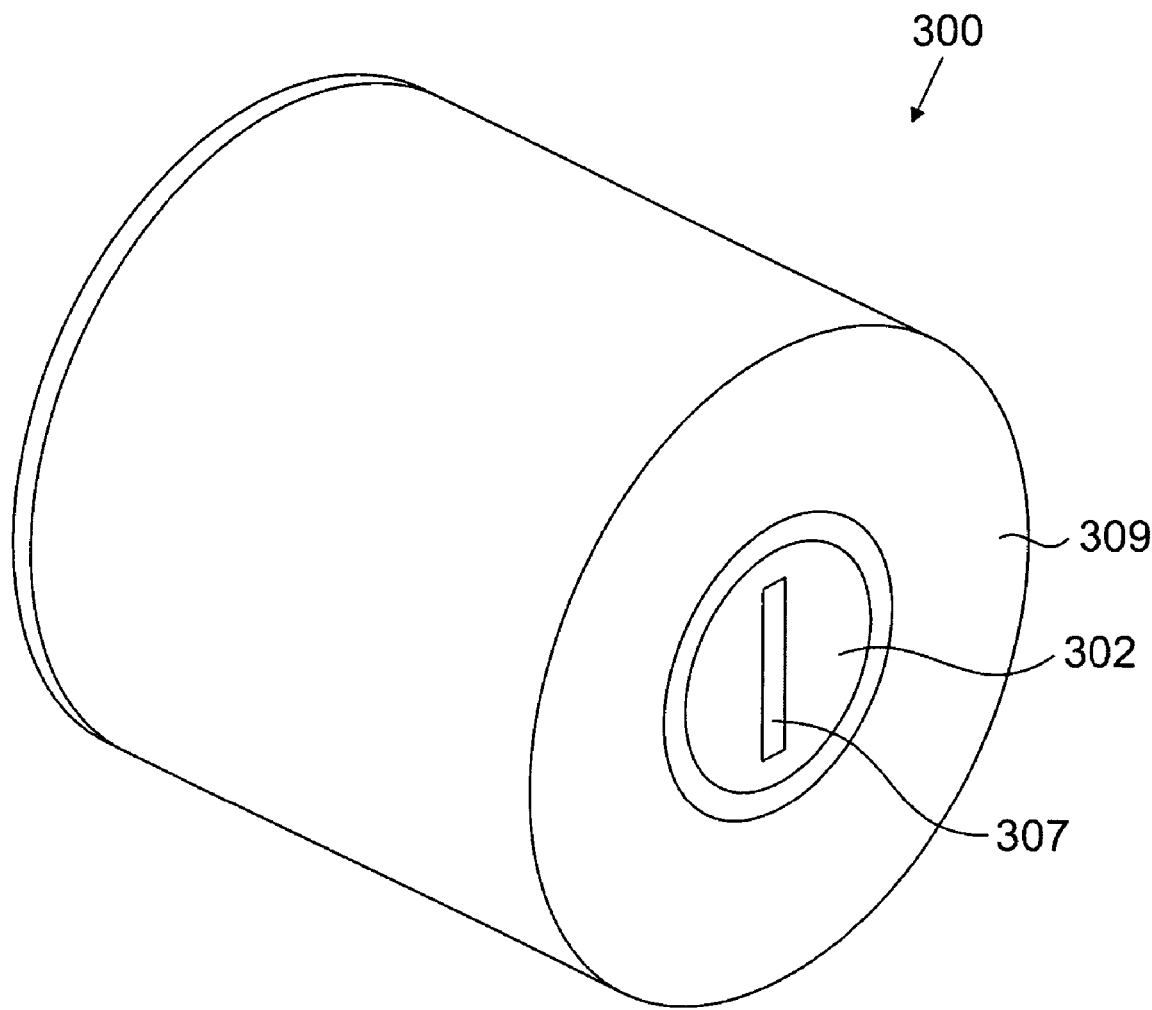
FIG. 4 is an example of a cylindrical X-ray head for use in an X-ray source, in accordance with an embodiment of the invention.
Figure 5:
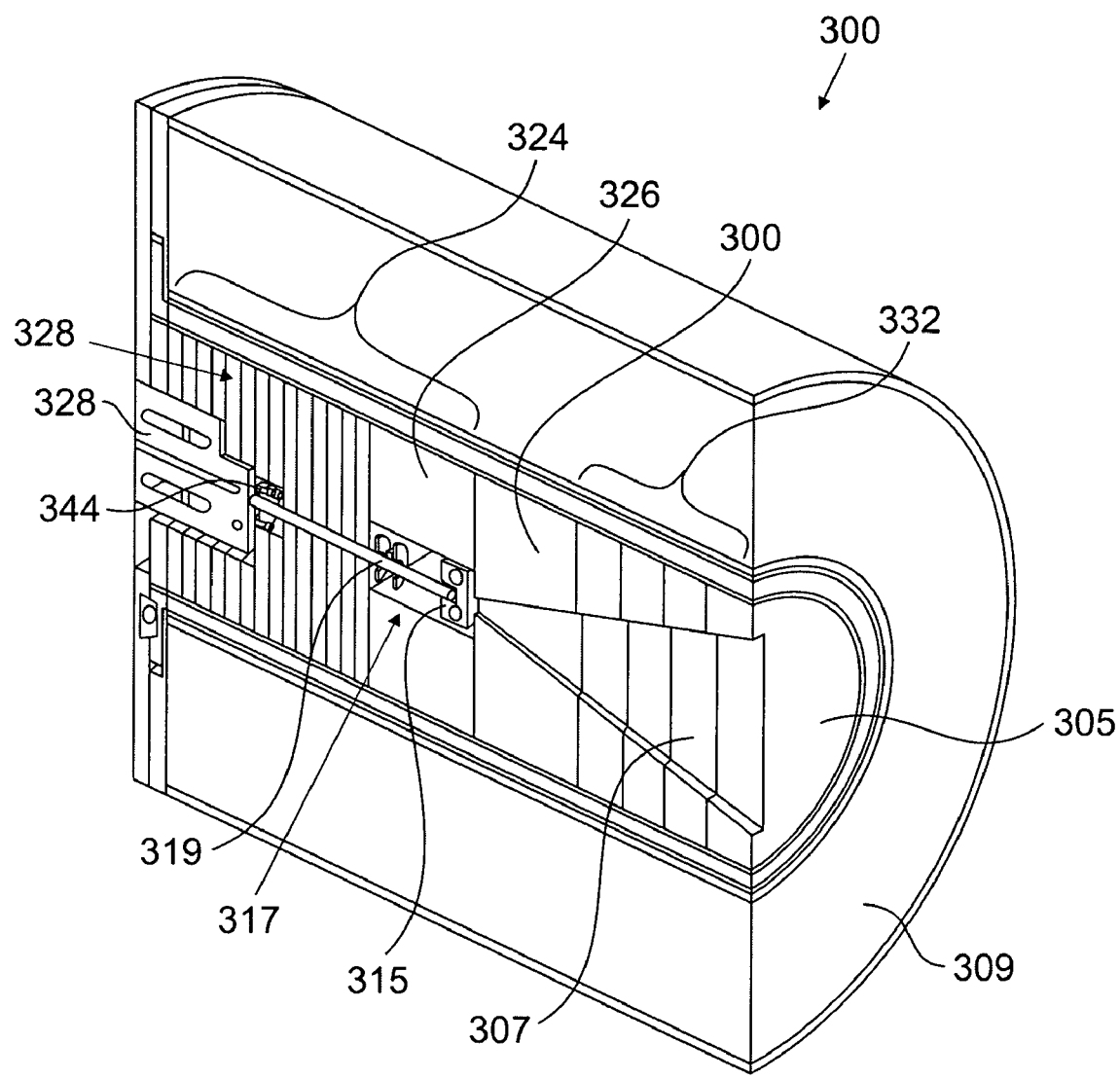
FIG. 5 is a cross-sectional, perspective view of the X-ray head of FIG. 4.
Figure 6:
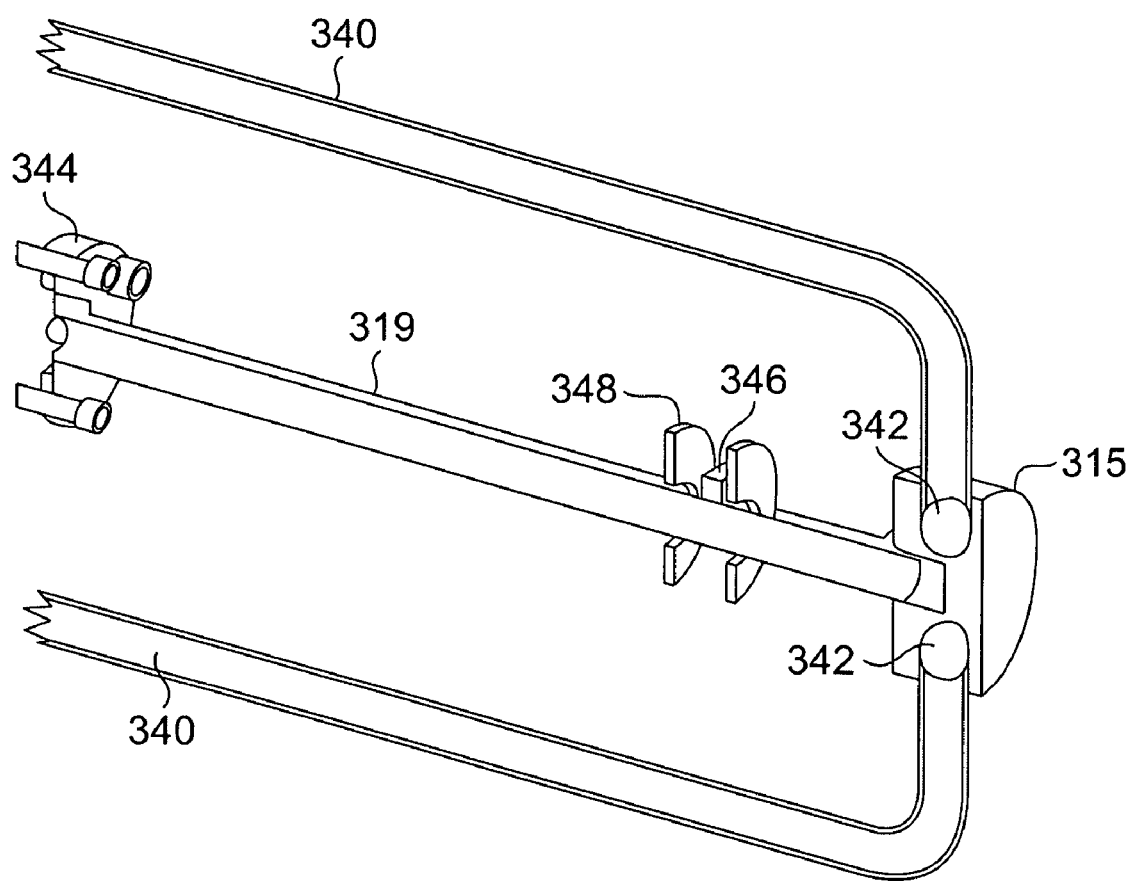
FIG. 6 is an enlarged cross-sectional view of the target assembly of FIG. 5.

In this example, the target shielding material 180 circumferentially surrounds the target 140, to prevent the escape of X-ray radiation in a direction perpendicular to the electron beam. Housing shielding 182 may be provided around the housing 110, if needed. The need for housing shielding 182 may depend on the accelerator design, the target shielding 180, and the required level of attenuation. If the accelerator uses a solenoid or otherwise narrowly focuses the electron beam on the target 140, and/or required attenuation is low, housing shielding may not be needed to shield stray electrons. If the target shielding 180 extends sufficiently behind the target, then the housing shielding 182 may not be needed to shield radiation emitted behind the target. The embodiment of FIGS. 4-6 shows such a design. In accordance with this embodiment of the invention, all or a portion of the target shielding 180 and the housing shielding 182, if present, also comprise isotopes of appropriate low Z materials having a neutron production threshold less than the peak acceleration energy of the source, to avoid the generation of neutrons by the shielding, although that is not required. Copper may be used, for example. The target shielding 180 and the housing shielding 182 may be a single piece or one or more separate pieces of material. The shielding materials 180 and 182 may be the same or different.

A collimator 190 is coupled to a distal end of the housing 110. It may be connected to the target shielding 182 and to the housing shielding 182, for example. The material of the collimator 190 defines a passage 195 to allow passage of the radiation 175. The passage is shaped to define the radiation beam 175. In accordance with this embodiment, all or a portion of the collimator 190 is composed of isotopes of a low Z material to avoid the generation of neutrons, although that is also not required. Copper may be used, for example. The collimator 190 may also comprise a single piece of material or multiple pieces.

The thicknesses of the shielding material 180, 182 and the collimator 190 may vary in different locations on the linear accelerator 100. At peak energies above 1 MeV, the intensity of the radiation emitted from the target is greatest in the forward direction, along the axis of the path of the electron beam 170 through the target 140. The intensity decreases as the angle from the axis increases. The collimator 190 may therefore be thicker than the shielding material 180, 182. The shielding material 180, 182 may also be thicker at angles closer to the axis, as is known in the art. When the target 140 is made of an appropriate low Z material, with a neutron production threshold above the peak acceleration energy of the source, the shielding 180, 182 and the collimator 190 need not be as thick as when the target is a high Z material because neutrons need not be shielded.

The different components of the source 100 may comprise different materials. For example, a natural copper target 140, a natural copper shielding 180a, 180b, and a natural iron collimator 190 may be used in an X-ray source 100 operating at a peak energy less than the neutron production threshold of iron-57 of 7.646 MeV.

A low Z material may have different stable isotopes with different neutron production thresholds. The isotopic composition of the low Z material therefore has to be considered when selecting appropriate materials for the target 140, shielding 180, 182, and collimator 190 to achieve a desired reduction or elimination of neutrons. To avoid all neutron production, the target 140, shielding 180, 182 and collimating materials 190 are selected such that the neutron production threshold for all isotopes exceeds the peak energy of the particular radiation source. In one example, naturally occurring copper comprises 69.17% of copper-63, which has a calculated neutron production threshold of 10.852 MeV, and 30.83% of copper-65, which has a calculated neutron production threshold of 9.910 MeV. Naturally occurring copper may therefore be used as a target 140, shielding 180, 182, and collimator 190 material for sources operating at a peak acceleration energy below 9.910 MeV, for zero neutron production. Isotopically pure copper-63 can be used as a target 140, shielding 180, 182, and collimator 190 material for sources operating at a peak acceleration energy below 10.852 MeV.

In another example, naturally occurring iron comprises 91.75% iron-56, having a calculated neutron production threshold of 11.197 MeV, 5.85% iron-54, having a calculated neutron production threshold of 13.37 MeV, 2.12% iron-57, having a calculated neutron production threshold of 7.646 MeV, and 0.28% iron-58, having a calculated neutron production threshold of 10.044 MeV. Hence, if naturally-occurring iron is used as a target 140, shielding 180, 182, and collimator 190, an X-ray source operating at a peak acceleration energy of less than 7.646 MeV will not generate neutrons. Isotopically pure iron shielding consisting of only iron- 56 could be used as a target 140, shielding 180a, 180b, and collimator 190 in X-ray sources 100 operating at peak acceleration energies up to 11.197 MeV without generating neutrons.

It is noted that if an iron target is used in an X-ray source operating up to (but less than) 10.044 MeV, only about 2.12% of the target 140, shielding 180, 182, and collimator 190 would generate neutrons. Therefore, at a peak energy of less than 10.044 MeV, a naturally occurring iron target 140, shielding 180, 182, and collimator 190 would provide a significantly reduced amount of neutron production, as compared to the use of tungsten, but would not eliminate it. If some amount of neutron generation may be tolerated, but less neutron generation is desired than if tungsten, tantalum, molybdenum, or lead are used, metals may be chosen that provide certain isotopes having neutron production thresholds below the peak energy of the source and certain isotopes having neutron production thresholds above the peak energy of the source. For example, in a source having a peak acceleration energy of 8.5 MeV, the following materials may be used for the target 140, the shielding 180, 182, and the collimator 190: magnesium (10% of which consists of magnesium-24 having a calculated neutron production threshold of 7.331 MeV), iron (2.12% of which consists of iron-57 having a calculated neutron production threshold of 7.646 MeV), nickel (3.63% of which consists of nickel-61 having a calculated neutron production threshold of 7.82 MeV), and zinc (4.10% of which consists of zinc-67 having a calculated neutron production threshold of 7.051 MeV). Different materials from this group may be used for the target 140, the shielding 180, 182, and the collimator 190. Such reductions could also be advantageous in particular applications. Shielding requirements may be reduced, for example.

In another example of a configuration that will reduce but not necessarily completely eliminate neutron production, certain components, such as the target 140, for example, may be an appropriate low Z material, while one or more other components, such as the collimator 190, the target shielding 180, and/or the housing shielding 182 may comprise high Z materials that may generate neutrons, such as tungsten, tantalum or lead, for example. Use of tungsten, tantalum, lead, or other such materials may provide better X-ray radiation generation or shielding, and may therefore be needed for certain components, or part of certain components, to meet performance and size requirements for the source, for example, as discussed below. Therefore, in accordance with another embodiment of the invention, neutron production is reduced by use of an appropriate low Z material for at least one but not necessarily all components, as compared to the use of tungsten, tantalum, molybdenum, or lead for that component.

Use of isotopically purified high Z atom material as a target 140, shielding 180, 182, and/or collimator 190 may also decrease or eliminate neutron generation, and provide some or all of the benefits of the use of a high Z material. For example, isotopically pure tungsten-182, which has a calculated neutron production threshold of 8.064 MeV, can be used in a source having a peak acceleration energy less than 8.064 MeV, without producing neutrons. Isotopically pure molybdenum-94, which has a peak acceleration energy of 9.677 MeV, can be used in a source having a peak acceleration energy less than 9.677 MeV, without producing neutrons. Mixtures of appropriate isotopes that are above the peak acceleration energy can be used, as well. For example, a mixture of molybdenum-96 and molybdenum-94 can be used in a source having a peak acceleration energy less than 8.064 MeV without producing neutrons.

While typically a metal, the target 140, shielding 180, 182, and/or the collimator 190 may be a non-metal, such as carbon. One stable isotope of carbon, carbon-13, which has an abundance of only 1.11%, has a calculated neutron production threshold of 8.071 MeV. The other stable isotope of carbon, carbon-12, which has an abundance of 98.89%, has a calculated neutron production threshold of 18.721 MeV. A source with a peak acceleration energy of less than 8.071 MeV would generate no neutrons, while in a source operating at above 8.071 and less than 18.721, only 1.11% of the carbon (the carbon-13) would generate neutrons. Preferably, a stable form of carbon is used, such as graphite or diamond, for example.

As is known in the art, the neutron production threshold for every isotope of a metal, including low atomic number metals, can be calculated according to the following equation:

$$\text{Threshold (MeV)} = (\text{Mass Excess } (Z, A-1) + \text{Neutron Mass Excess}) - \text{Mass Excess } (Z, A).$$

In the equation above, Z is an atomic number of an atom of an element; A is a mass number (sum of the number of protons and neutrons) of an atom of the element; (Z, A) is an original isotope of an atom of the element (before it loses a neutron as a result of interacting with an X-ray radiation); and (Z, A−1) is a mass of an atom of a resulting isotope of the element after loss of one neutron. Mass Excess (Z, A−1) is the equivalent energy of the mass of the resulting isotope, as compared to carbon-12, which has a mass excess of 0 MeV. The Neutron Mass Excess is a constant equal to 8.071 MeV, which is the energy of the difference between the neutron mass of a particular isotope and the neutron mass of carbon-12, which is set at 0 MeV. The Mass Excess (Z, A) is the equivalent energy of the mass excess of the initial isotope. Mass instead of Mass Excess may be used to determine the threshold as well, as is known in the art.

For example, the neutron production threshold for magnesium-24 is calculated as follows. Magnesium-24 is an original isotope which, after interaction with a beam of X-ray photons, emits one neutron and becomes magnesium-23, a resulting isotope. The mass excess (Z, A−1) of magnesium-23 (−5.473 MeV) is added to neutron mass excess (8.071 MeV). The mass excess (Z, A) of magnesium-24 is then subtracted (−13.933 MeV), yielding a neutron production threshold of 16.531 MeV, as shown below:

$$(-5.473 \text{ MeV} + 8.071 \text{ MeV}) - (-13.933 \text{ MeV}) = 16.531 \text{ MeV}.$$

Large negative mass excesses (Z, A) show that the protons and neutrons in a nucleus of an atom are tightly bound together. An amount of external energy exceeding the absolute value of the negative mass excess is necessary to remove one neutron from the nucleus. In other words, the neutron production threshold of a particular isotope is a minimum energy a photon needs to have to emit one neutron from a nucleus of that isotope.

Calculated neutron production thresholds for each isotope of several materials are summarized in Table I, below. In Table I, some abundances may not add to 100%, due to round off errors. Abundance information is not provided for unstable isotopes. Neutron production thresholds for isotopes of elements ranging from beryllium to uranium may also be found in Neutron Contamination from Medical Electron Accelerators, National Council on Radiation Protection and Measurements, Bethesda, Md., pp. 18-23 (1995), where they are referred to as "separation energies."

TABLE I

| Element/Isotope | Atomic Number | Mass Excess (MeV) | Neutron Production Threshold (MeV) | Abundance (%) |
|---|---|---|---|---|
| Beryllium-8 | 4 | 4.942 | | |
| Beryllium-9 | 4 | 11.348 | 1.665 | 100.00% |
| Carbon-11 | 6 | 10.650 | | |
| Carbon-12 | 6 | 0 | 18.721 | 98.89% |
| Carbon-13 | 6 | 3.125 | 8.071 | 1.11% |
| | | | | 100.00% |
| Magnesium-23 | 12 | −5.473 | | |
| Magnesium-24 | 12 | −13.933 | 16.531 | 78.99% |
| Magnesium-25 | 12 | −13.193 | 7.331 | 10.00% |
| Magnesium-26 | 12 | −16.215 | 11.093 | 11.01% |
| | | | | 100.00% |
| Aluminum-26 | 13 | −12.210 | | |
| Aluminum-27 | | −17.197 | 13.058 | 100.00% |
| Scandium-44 | 21 | −37.816 | | |
| Scandium-45 | 21 | −41.069 | 11.324 | 100.00% |
| Titanium-45 | 22 | −39.007 | | |
| Titanium-46 | 22 | −44.125 | 13.189 | 8.25% |
| Titanium-47 | 22 | −44.932 | 8.878 | 7.44% |
| Titanium-48 | 22 | −48.487 | 11.626 | 73.72% |
| Titanium-49 | 22 | −48.558 | 8.142 | 5.41% |
| Titanium-50 | 22 | −51.426 | 10.939 | 5.18% |
| | | | | 100.00% |
| Vanadium-49 | 23 | −47.956 | | |
| Vanadium-50 | 23 | −49.218 | 9.333 | 0.25% |
| Vanadium-51 | 23 | −52.198 | 11.051 | 99.75% |
| | | | | 100.00% |
| Chromium-49 | 24 | −45.326 | | |
| Chromium-50 | 24 | −50.255 | 13 | 4.35% |
| Chromium-51 | 24 | −51.445 | | |
| Chromium-52 | 24 | −55.413 | 12.039 | 83.79% |
| Chromium-53 | 24 | −55.281 | 7.939 | 9.50% |
| Chromium-54 | 24 | −56.929 | 9.719 | 2.37% |
| | | | | 100.01% |
| Manganese-54 | 25 | −55.552 | | |
| | 25 | −57.707 | 10.226 | 100.00% |
| Iron-53 | 26 | −50.941 | | |
| Iron-54 | 26 | −56.249 | 13.379 | 5.85% |
| Iron-55 | 26 | −57.475 | | |
| Iron-56 | 26 | −60.601 | 11.197 | 91.75% |
| Iron-57 | 26 | −60.176 | 7.646 | 2.12% |
| Iron-58 | 26 | −62.149 | 10.044 | 0.28% |
| | | | | 99.99% |
| Cobalt-58 | 27 | −59.842 | | |
| Cobalt-59 | 27 | −62.224 | 10.453 | 100.00% |
| Nickel-57 | 28 | −56.076 | | |
| Nickel-58 | 28 | −60.223 | 12.218 | 68.08% |
| Nickel-59 | 28 | −61.151 | 8.999 | 26.22% |
| Nickel-60 | 28 | −64.468 | 11.388 | 1.14% |
| Nickel-61 | 28 | −64.217 | 7.82 | 3.63% |
| Nickel-62 | 28 | −66.743 | 10.597 | 0.93% |
| | | | | 100.00% |
| Copper-62 | 29 | −62.795 | | |
| Copper-63 | 29 | −65.576 | 10.852 | 69.17% |
| Copper-64 | 29 | −65.421 | | |
| Copper-65 | 29 | −67.260 | 9.910 | 30.83% |
| | | | | 100.00% |
| Zinc-63 | 30 | −62.210 | | |
| Zinc-64 | 30 | −66.000 | 11.861 | 48.60% |
| Zinc-65 | 30 | −65.908 | | |
| Zinc-66 | 30 | −68.897 | 11.06 | 27.90% |
| Zinc-67 | 30 | −67.877 | 7.051 | 4.10% |
| Zinc-68 | 30 | −70.004 | 10.198 | 18.80% |
| Zinc-69 | 30 | −68.415 | | |
| Zinc-70 | | −69.560 | 9.216 | 0.60% |
| | | | | 100.00% |
| Molybdenum-91 | 42 | −82.210 | | |
| Molybdenum-92 | 42 | −86.806 | 12.667 | 14.84% |
| Molybdenum-93 | 42 | −86.805 | | |
| Molybdenum-94 | 42 | −88.411 | 9.677 | 9.25% |
| Molybdenum-95 | 42 | −87.709 | 7.369 | 15.92% |
| Molybdenum-96 | 42 | −88.792 | 9.154 | 16.68% |
| Molybdenum-97 | 42 | −87.542 | 6.821 | 9.55% |
| Molybdenum-98 | 42 | −88.113 | 8.642 | 24.13% |
| Molybdenum-99 | 42 | −85.967 | | |
| Molybdenum-100 | 42 | −86.185 | 8.289 | 9.63% |
| | | | | 100.00% |
| Tantalum-180 | 73 | −48.861 | | |
| Tantalum-181 | 73 | −48.441 | 7.651 | 99.99% |
| Tungsten-179 | 74 | −49.300 | | |
| Tungsten-180 | 74 | −49.644 | 8.415 | 0.12% |
| Tungsten-181 | 74 | −48.253 | | |
| Tungsten-182 | 74 | −48.246 | 8.064 | 26.50% |
| Tungsten-183 | 74 | −46.366 | 6.191 | 14.31% |
| Tungsten-184 | 74 | −45.706 | 7.411 | 30.64% |
| Tungsten-185 | 74 | −43.389 | | |
| Tungsten-186 | 74 | −42.512 | 7.194 | 28.43% |
| | | | | 100.00% |
| Lead-203 | 82 | −24.805 | | |
| Lead-204 | 82 | −25.124 | 8.394 | 1.40% |
| Lead-205 | 82 | −23.784 | | |
| Lead-206 | 82 | −23.801 | 8.088 | 24.10% |
| Lead-207 | 82 | −22.467 | 6.737 | 22.10% |
| Lead-208 | 82 | −21.764 | 7.368 | 52.40% |
| | | | | 100.00% |

Figure 2:
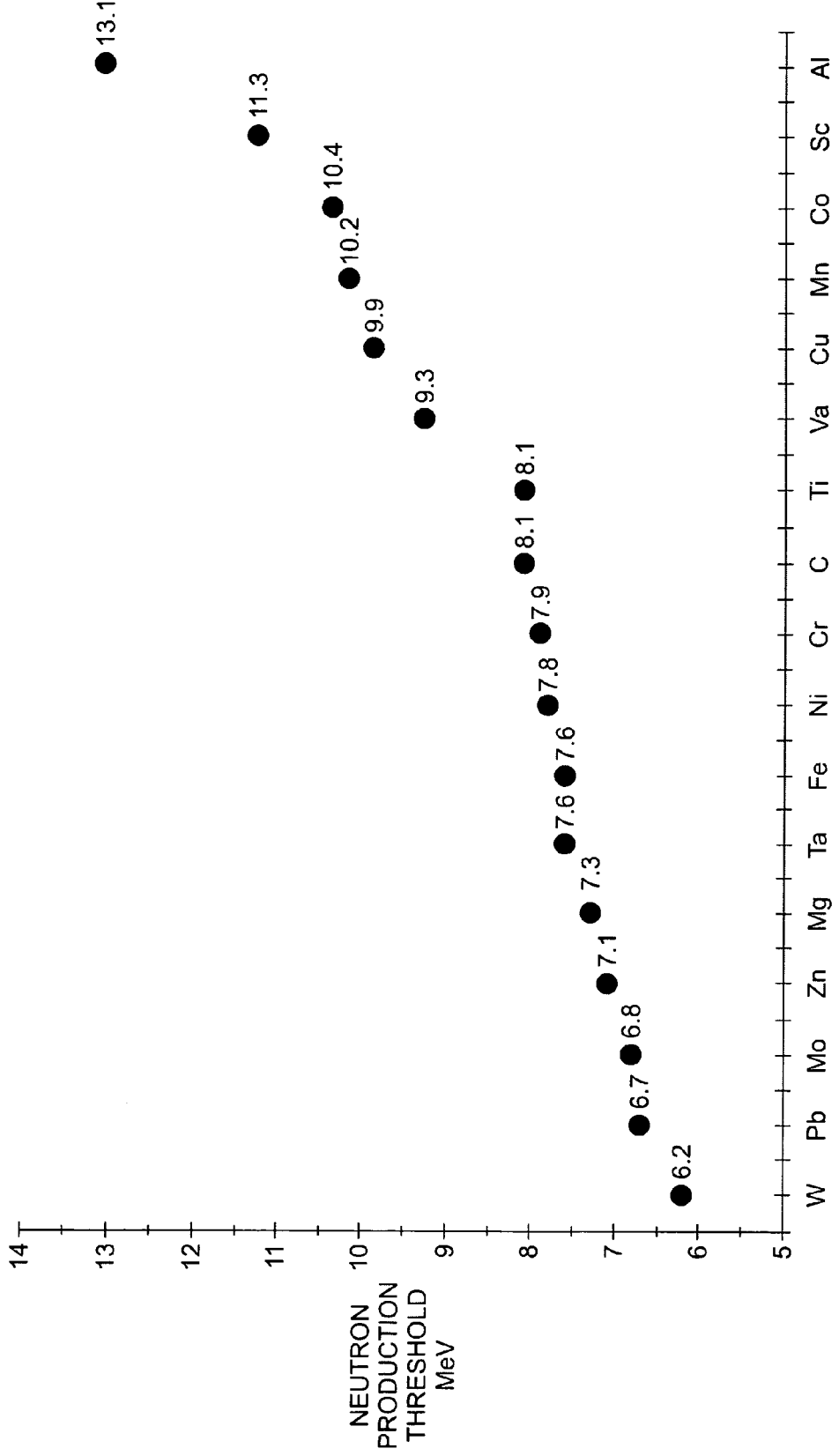
FIG. 2 is a graph showing the neutron production thresholds for isotopes with the lowest threshold, for a number of materials.

FIG. 2 is a graph showing the lowest neutron production thresholds among isotopes of a number of materials presented in the table above. In FIG. 2, the neutron production thresholds from Table I are rounded off to the nearest tenth. In an X-ray source 100 comprising a target 140, shielding 180, 182, and a collimator 190 of a selected material (naturally occurring), whose lowest peak acceleration energy is above each of these thresholds, no neutrons would be produced. For example, the lowest calculated neutron production threshold for copper is 9.910 MeV. Any source with a copper target 140, shielding 180, 182, and collimator 190 operating below 9.910 MeV would not generate neutrons during operation.

In another example, as shown in the table above and in FIG. 2, if no or reduced neutron production (as compared to tungsten) is desired in an X-ray source 100 operating at a peak acceleration energy up to 7 MeV, the following naturally occurring low Z materials are appropriate for the target 140, the shielding 180, 182, and/or the collimator 190: carbon, magnesium, aluminum, scandium, titanium, vanadium, chromium, manganese, iron, cobalt, nickel, copper, and zinc.

In another example, if no or reduced neutron production (as compared to tungsten) is desired in an X-ray source 100 with a peak acceleration energy in a range of from 7 MeV to 8 MeV, the following naturally occurring low Z materials are appropriate for the target 140, the shielding 180, 182, and/or the collimator 190: carbon, aluminum, scandium, titanium, vanadium, manganese, cobalt, and copper.

In another example, if no or reduced neutron production (as compared to tungsten) is desired in an X-ray source 100 with a peak acceleration energy in a range of from 8 MeV to 9 MeV, the following naturally occurring low Z materials may be used for the target 140, the shielding 180, 182, and/or the collimator 190: aluminum, scandium, vanadium, manganese, cobalt, and copper. Radiation sources for use in scanning cargo conveyances often have a peak acceleration energy of 9 MeV to generate radiation with a peak energy of 9 MeV. 9 MeV is sufficient to penetrate most cargo conveyances, including standard cargo conveyances, regardless of the contents. Copper is a preferred material for use at peak acceleration energies of less than 9.910 MeV, including 9 MeV.

In another example, if no or reduced neutron production (as compared to tungsten) is desired in an X-ray source 100 with a peak acceleration energy in a range of from 9 MeV to 10

MeV, the following naturally occurring materials may be used for the target 140, the shielding 180, 182, and/or the collimator 190: aluminum, scandium, and cobalt.

At a peak acceleration energy in a range of from 10 MeV to 11 MeV, scandium and aluminum may be used and at a peak acceleration energy in a range of from 11 MeV to 13 MeV, aluminum may be used.

In addition to the neutron production threshold, manufacturability and performance are other considerations in the selection of a target, collimator, and/or shielding materials. For example, the thermal conductivity, melting point, fatigue, ability to braze and bond, ability to vacuum seal, of particular materials, are important considerations. For target materials, the ability to generate Bremsstrahlung X-ray radiation and the quantity generated, are also a consideration. Copper meets many of these considerations, and is, therefore, a preferred low Z material.

For example, the target may be GlidCop® AL-60 Dispersion Strengthened Copper, available from OMG Americas, Newark, N.J., for example. GlidCop® AL-60 is said to comprise 98.9% by weight naturally occurring copper and 1.1% by weight aluminum oxide ($Al_2O_3$). It is said to have has a thermal conductivity of 322 watts/meter-kelvin, a tensile strength of 413-517 MPa, and electrical resistivity of 2.2e-006 ohm-cm. Oxygen-free Electronic Copper, UNS C10100, which is available from Hitachi Metals, Ltd, Japan, and Copper and Brass Sales, Southfield, Mich., for example, may be used for target shielding 220. UNS C10100 is said to be at least 99.99% by weight copper. Its density is said to be 8.89-8.94 g/cc and its Vickers hardness is said to be 75-90. A lower grade copper may be used for the collimator 190.

Since low Z materials typically absorb fewer X-ray photons than an equal volume of the high Z materials, a greater volume of low Z shielding is necessary to absorb the same amount of photons. However, since the low Z materials have lower density than high Z materials, the weight of the radiation inspection system may remain almost the same as a system with the high Z material shielding. The thickness of shielding necessary to absorb a particular amount of photons having a particular energy level is calculated according to the following equation, for a point source emitting isotropically:

$$I(t)=I_0\exp(-\mu*t)/(4\pi R^2),$$

where t is the thickness of a shielding material between the source and the measurement point, I(t) is the intensity of the radiation after passing through the shielding material having the thickness t, $I_0$ is the initial intensity of the radiation, $\mu$ is the X-ray attenuation coefficient, and R is the distance between the source and measurement point. As is known in the art, a broadbeam tenth value layer table for the material comprising the shield may be used to calculate $\mu$ for the material, at a particular energy.

When an appropriate low Z material is used as the target 140 of the radiation source 100 to prevent or reduce neutron production, the probability of X-ray photon emission will be less than that of a high Z material, for each accelerated electron that hits the target. To compensate for this natural phenomenon, more electrons may be accelerated into the target 140.

The absorption of neutrons by low Z shielding may reduce or eliminate the number of neutrons available to activate materials (generate X-ray radiation) due to neutron capture by other components of the X-ray scanning system, depending on the shielding material, as is known in the art. Shielding a radiation inspection system with a neutron-absorbing material facilitates use of such systems as mobile systems as opposed to stationary systems of prior art.

Figure 3:
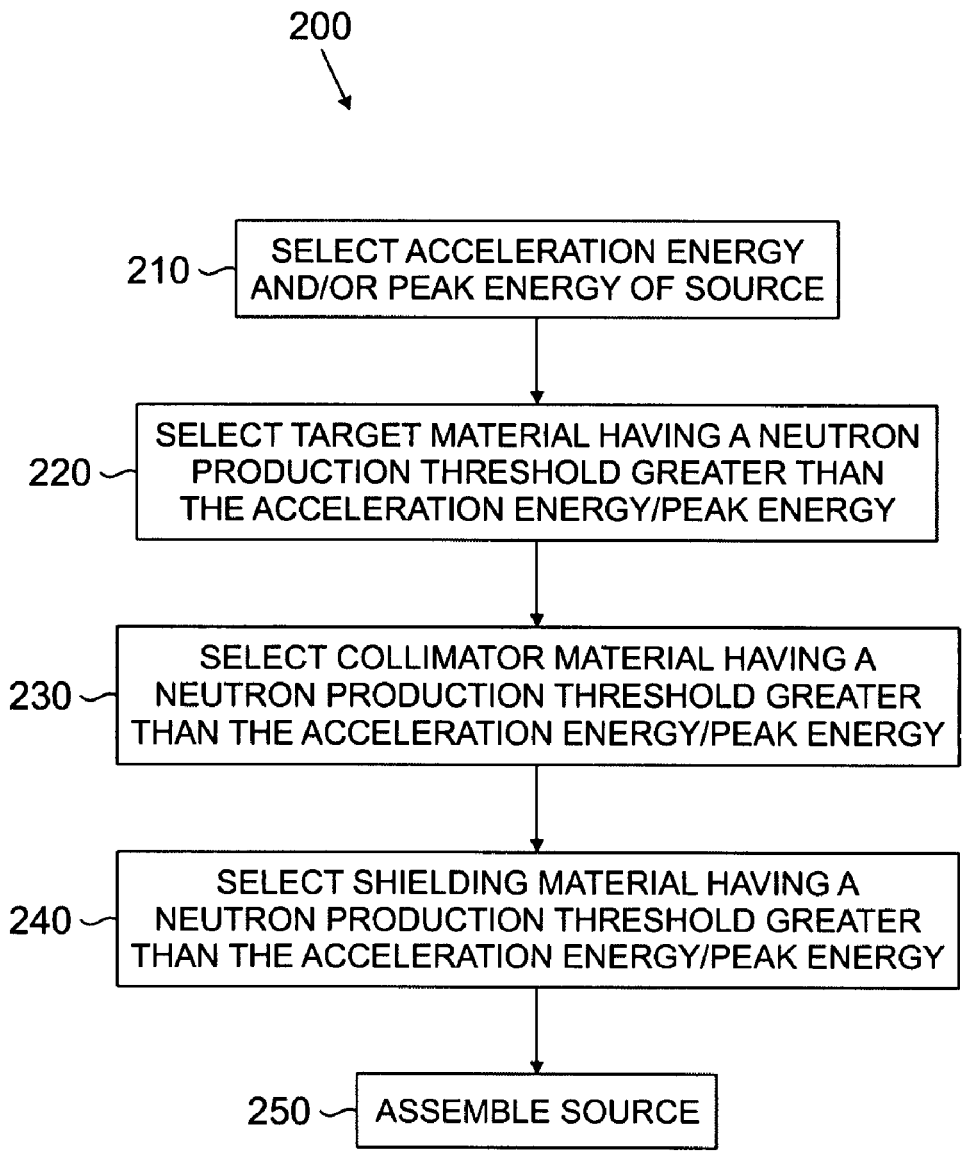
FIG. 3 is an example of a method of manufacturing an X-ray radiation source with no neutron production, in accordance with an embodiment of the invention.

FIG. 3 is an example of a method 200 of manufacturing an X-ray radiation source with no neutron production in accordance with an embodiment of the invention. A desired peak acceleration energy and/or peak radiation energy of a source is selected, in Step 210. A target material having a neutron production threshold less than the peak acceleration energy or the peak radiation energy is selected, in Step 220. Shielding material having a neutron production threshold less than the acceleration energy is selected, in Step 230. A collimator material having a neutron production threshold less than the acceleration energy is selected, in Step 240. The source is assembled with the selected material or materials, in Step 210. Steps 220, 230 and 240 may be selected in any order. The same or different materials may be selected for each component. The material for each component may be selected based on a table of neutron production thresholds such as the table of Table I, a graph as in FIG. 2, or calculations, as described above, for example.

If there are no size, weight, and/or cost constraints with respect to the X-ray source 100, the target 140, shielding 180, 182 and the collimator 190 may all consist essentially of a material or materials whose neutron production threshold is less than the peak acceleration energy of the source. However, the amount of low Z material, such as copper, needed to provide X-ray and neutron shielding and X-ray collimation, for example, may take up a volume about twice as large as tungsten, and would cost more than the use of tungsten. The size, weight, and cost differences for other low Z materials are comparable.

In a particular application, size, weight, and cost considerations may therefore need to be balanced against the value of a reduction or elimination of neutron production. Materials both above and below the neutron production threshold may be needed to meet the requirements for X-ray production, neutron production, size, weight, and/or cost in a particular application. FIG. 4 shows an example of a cylindrical X-ray head 300 for use in an X-ray source in accordance with an embodiment of the invention, designed to meet predetermined neutron production and size requirements in a source with a predetermined acceleration energy. For example, the X-ray head may be designed to produce up to a predetermined amount of neutrons per hour (which is less than would be produced if tungsten were used) at a peak acceleration energy of 9 MeV, and to encompass a predetermined volume (which is less than the volume required if the target, shielding and collimator were to be made of only copper). To meet the volume and neutron production requirements, the X-ray head comprises a combination of copper, tungsten, and lead. In FIG. 4, a collimator 305 is shown surrounded by lead shielding 309. In this example, the collimator defines a passage 306 to define a fan beam of radiation.

FIG. 5 is a cross-sectional, perspective view of the X-ray head 300 of FIG. 4. The X-ray head 300 comprises a copper target disk 315 within a target assembly 317. The target assembly 317 also comprises a drift tube 319 extending from a guide front end 321 to the target 315. The guide front end 321 is coupled to an output of an acceleration chamber of a linear accelerator, for example, in use. Electrons accelerated by an acceleration chamber enter the drift tube 319 and collide with the target 315. The target 315 may be thick enough to stop all electrons.

A target assembly shielding 324 is provided around the target assembly 317 to attenuate the escape of X-ray radiation from the target 315 in directions perpendicular to the electron beam and behind the target. The target assembly shielding 324 comprises a first target assembly shielding section 326 of copper in the form of a cylinder around the target assembly 317, and a second target assembly shielding section 328 of tungsten behind the target assembly 317. In this example, the first target assembly shielding section 326 comprises a tenth value layer ("TVL") of copper, which is sufficient to attenuate X-ray radiation by 10%. Additional sections of different materials may be provided, as well.

The collimator 305 shown in FIG. 4 is downstream of the target 315 in FIG. 5. The collimator 305 comprises a first, upstream collimator section 330 of copper and a second, downstream collimator section 332 of tungsten. The upstream collimator section 330 also comprises a TVL of copper. The first and second sections 330, 332 are cylinders with matching outwardly tapered inner diameters forming the passage 307, also shown in FIG. 4, shaped to define the radiation beam in this example. The second collimator section 332 may comprise a plurality of tungsten disks for ease of manufacture and assembly. Multiple passages may be defined, as well. Additional sections of different material may be provided, as well.

The passage 307 may be shaped to define a cone beam, a pencil beam, or other such desired shape, as well. The collimator 305 impedes the escape of X-ray radiation in directions forward of the target 315, outside of the passage 307.

The lead shielding 310, also shown in FIG. 4, encases the target assembly shielding 217, the collimator 305, and the upstream target assembly shielding 324. Sufficient tungsten in the second target assembly shielding section 32 and in the second collimator section 332, as well as lead shielding 310 are provided to meet space and X-ray leakage requirements for a particular application.

FIG. 6 is an enlarged cross-sectional view of the target assembly 317 of FIG. 5, showing the copper disk 315 and the drift tube 319. Cooling tubes 340 are also shown. Openings 342 are provided in the target 315 to receive cooling fluid provided by the cooling tubes 340, as is known in the art. A downstream end of the drift tube 319 extends partially into the target 315. A metallic vacuum sealing flange 344, such as a Conflat® mount, available from Varian Inc., Palo Alto, Calif., or MDL Vacuum Products Corporation, Hayward Calif. is provided at one end of the drift tube, to form a vacuum seal in the target assembly 317, as is known in the art. A target insulator 346 is provided around the drift within the first target assembly shielding section 326 of copper tube 319. A flexure 348 of soft material, such as copper is also provided around the drift tube 319, to compensate for tolerance errors, as is known in the art.

The X-ray head 300 is coupled to the forward end of a linear accelerator, for example. An example of suitable linear accelerator 100 is shown in FIG. 1. The X-ray head 300 may be attached to the downstream end of the linear accelerator 100, instead of the target 140 and target shielding 180. An upstream end of the drift tube 319 is coupled to an output of the acceleration chamber, such as the acceleration chamber 120 in FIG. 1, with the desired acceleration energy. During operation, electrons generated by the electron gun 150 are accelerated, as discussed above. The accelerated electrons enter the drift tube 319 and impact the copper target 315. Bremsstrahlung X-ray radiation with a peak energy of 9 MeV is generated as the copper target 315 decelerates the electrons of the electron beam. Since the peak acceleration energy of the linear accelerator 100 (9 MeV) is less than the lowest neutron production threshold of the copper target 315 (9.910 MeV), no neutrons will be produced by the target 315.

X-ray radiation emitted forward of the target 315 is collimated into a desired shape, here a fan beam, by the passage 307 (see FIGS. 4 and 5). Much of the forward emitted radiation that does not pass through the passage 307 is absorbed by the first collimator section 330 of copper. Since copper has a neutron production threshold less than the peak acceleration energy of the source and of the generated X-ray radiation, no neutrons are produced. Much of the remaining radiation is absorbed by the second collimator section 332 of tungsten. While that X-ray radiation may cause the generation of neutrons by the second collimator section 340 of tungsten, since the amount of X-ray radiation reaching the second section has already been reduced by the first section 335, many fewer neutrons are produced than if the entire collimator were to be of tungsten, tantalum, or lead, for example, as in the prior art. If the entire collimator 305 is copper, while no neutrons would be generated, to have the same shielding efficiency, for X-ray radiation, the collimator 305 would have to be much larger.

As indicated above, about 10% of the X-ray radiation emitted by the target 315 towards the first target assembly shielding 326 of copper will be absorbed by the TVL of copper shielding. Neutrons will not be generated, for the same reason discussed above. Much of the radiation that passes through the target assembly shielding 326 will be absorbed by the lead housing 310 and the second target assembly shielding 328 of tungsten. Small leakage may be tolerated. While neutrons may be generated by the lead and tungsten, which have neutron production thresholds below the peak energy of the radiation, the X-ray radiation is so attenuated, that the neutron generation will be low—much lower than if the target and shielding were all tungsten, tantalum, or lead. In addition, the radiation emitted to the rear of the target 315 is of much lower intensity than that emitted forward of the target. While copper could be used in the rear target assembly shielding instead of tungsten, much more copper would be required to achieve the same shielding efficiency as the tungsten, as discussed above. An overall reduction in neutron production of up to 100% may be achieved depending on the allowable space.

It is noted that due to the design of the X-ray head 300, housing shielding, such as housing shielding 182 in FIG. 1, may not be required to shield X-ray radiation emitted in a direction behind the target 315, because sufficient shielding is provided by the X-ray head 300. The accelerator design may also obviate the need for housing shielding to shield stray electrons, as discussed above. If housing shielding is used, it may also be an appropriate low Z material, such as copper, for example. In addition, a combination of a low Z material, such as copper, and a high Z material, such as tungsten, may also be provided if needed in a particular application.

Isotopes of tungsten and molybdenum that will not generate neutrons at the peak acceleration energy of the source may also be used instead of or along with copper and other materials in the target 315 and the other components of the X-ray head 300.

A source 100 or X-ray head 300 may be developed to meet acceleration energy, X-ray production, neutron production, size, weight, and cost requirements with the assistance of a Monte Carlo or other such random event simulation, in an iterative process. An MCNP5 Monte Carlo simulation, available from Oak Ridge National Laboratories, Oak Ridge, Tenn., for example, may be used. Other source configurations to meet other requirements may be similarly developed by those skilled in the art with Monte Carlo or other such simulations, and the teachings of the present invention.

Figure 7:
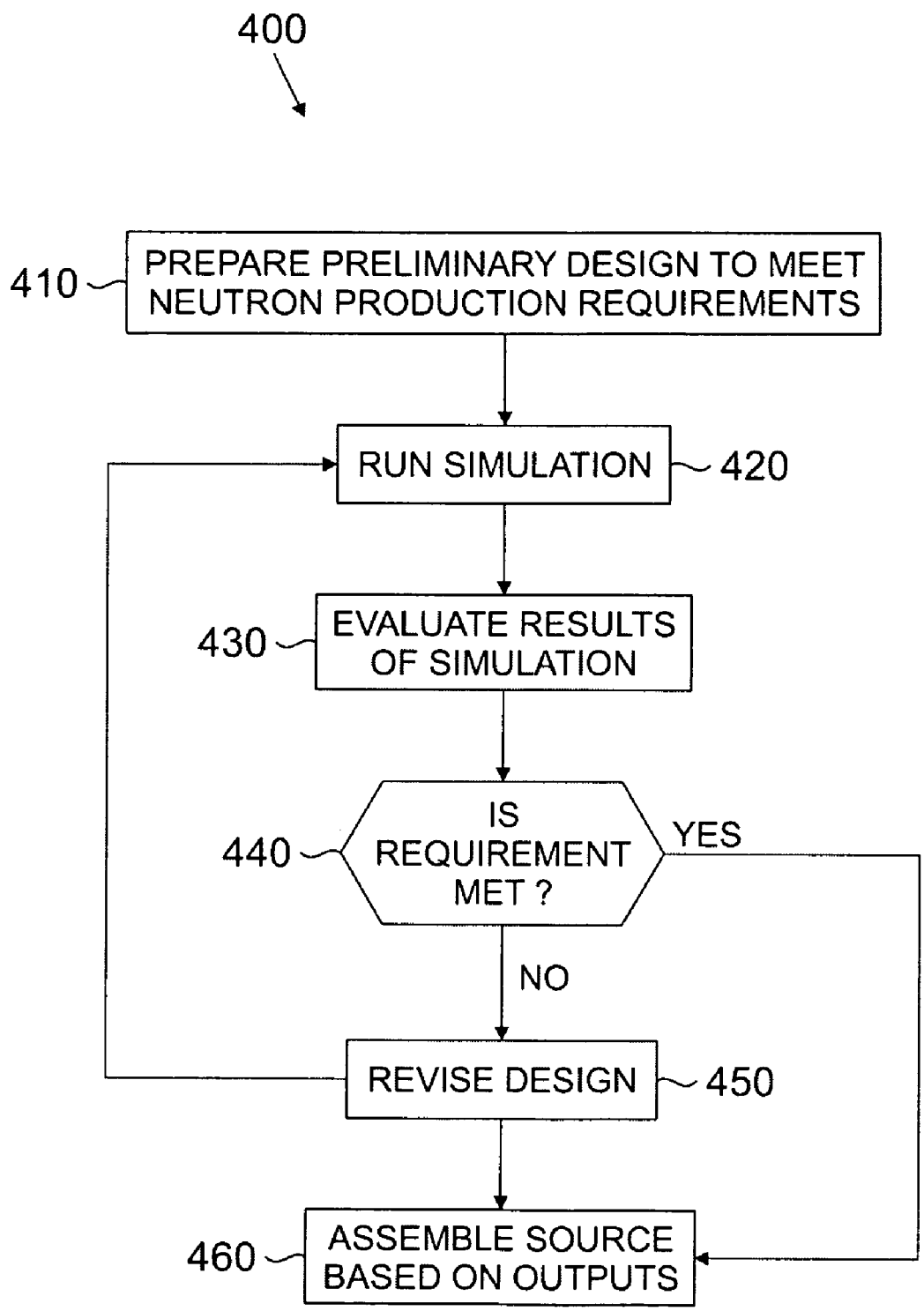
FIG. 7 is an example of an iterative process to design a source in accordance with another embodiment of the invention.

An example of an iterative process 400 to design a source in accordance with another embodiment of the invention is shown in FIG. 7. A first, preliminary design is prepared to meet maximum neutron production requirements, in Step 410. The design may be made to meet other requirements as well, such as X-ray production levels, size, and weight, for example. Assuming that it is known that use of copper for the target, collimator and shielding will result in a source greater than the allowable size, and that predetermined amount of neutron production is acceptable, the first, preliminary design may comprise a copper target, a tungsten target assembly shielding, a tungsten collimator, a tungsten upstream target assembly shielding, and lead shielding, for example, of predetermined sizes. A simulation, such as a Monte Carlo simulation, is run, in Step 420, to determine the expected neutron production resulting from the preliminary design. The expected level of X-ray production may also be determined. The results of the simulation are evaluated, in Step 430. If the requirements are met, the source may be assembled based on the design, in Step 440. If the requirements are not met, then the design is revised based on the results of the simulation, in Step 450. For example, if the results of the simulation in Step 440 show that there would be too much neutron production, then all or part of the tungsten target assembly shielding may be made of copper. The simulation is run again, in Step 420, and the results evaluated, in Step 430. If the simulation shows that the neutron production is still too high, another revised design may be prepared. In the next revised design, a portion of the collimator closest to the target may be made of copper for example. Steps 420-450 may be repeated until the neutron production requirements and other requirements, if present, are met. The simulation facilitates testing of minor adjustments in design and dimensions to achieve a final design, as well.

Figure 8:
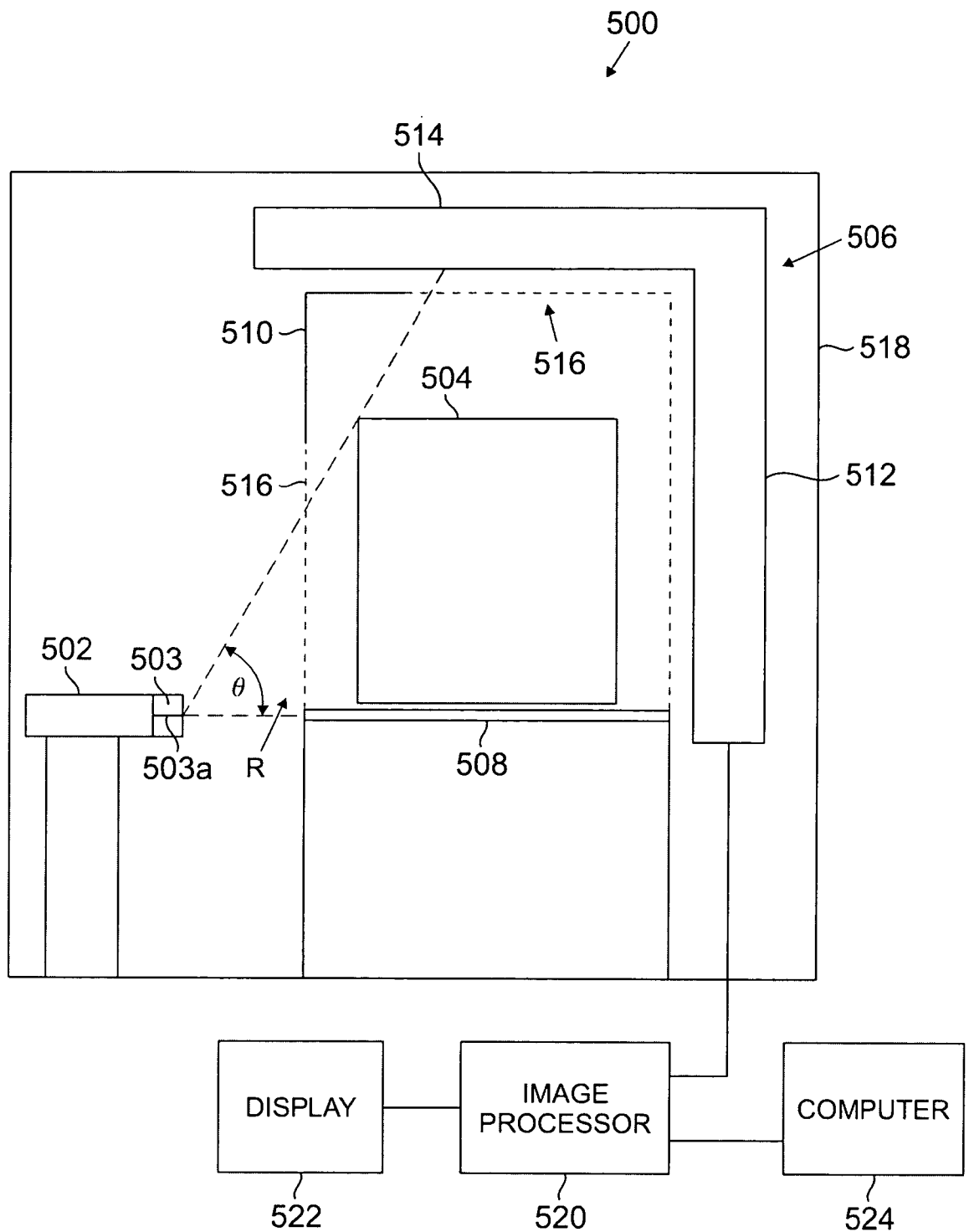
FIG. 8 is a front view of a cargo scanning system, in accordance with an embodiment of the invention.

A radiation source in accordance with embodiments of the invention may be used in a radiation inspection system, such as a cargo scanning system 500 depicted in FIG. 8, for example, in accordance with another embodiment of the invention. An X-ray source 502, which may be similar to the source 100 of FIG. 1 and/or may include the X-ray head 300 of FIGS. 4-6, for example, is shown on one side of a cargo conveyance 504. The cargo conveyance 504 may be a standard cargo conveyance, which has a width of about 6-9 feet (1.8-2.7 meters) or other sized cargo conveyance. The source and system of embodiments of the invention may be particularly useful with cargo conveyances with thicknesses of 5 feet (1.5 m) or more, since higher energy radiation beams are required to penetrate the thickness. For example, the peak acceleration energy of the source may be at least about 6.2 MeV, at least about 6.7 MeV, or at least about 7.7 MeV, to generate radiation having a peak (maximum) energy of at least about 6.2 MeV, 6.7 MeV, or 7.7 MeV, respectively, depending on the configuration. The peak acceleration energy may be about 9 MeV, for example.

The source 502 includes a collimator 503. A slot 503a is provided through the collimator 503 to define the radiation beam R. A detector 506 is supported on an opposite side of the cargo conveyance 504, to detect radiation interacting with the cargo conveyance. The detector 506 may be positioned to detect radiation transmitted through the cargo conveyance 504, for example. The cargo container 504 is conveyed by a conveyor system 508 through a shielded tunnel 510, between the source 502 and the detector 506. The detector 506 may be an L-shaped detector array, with a first arm 512 behind the tunnel and a second arm 514 over the top of the tunnel, for example. A linear or other shaped detector array may be used, as well.

The tunnel 510 has windows 516 to allow for the passage of an X-ray radiation beam R. Shielding walls 518 surround the source 502, the detector 506, and a portion of the conveying system 508. Concrete is a preferred shielding material for both neutrons and X-rays. If space or other requirements prevent the use of concrete, then a multi-layer shield may be used. For example, polyethylene may be used as an inner layer to shield neutrons and lead or steel may be used as an outer layer to shield X-rays. The outer layer also shields gamma rays emitted by the polyethylene. Openings (not shown) are provided in the shielding walls 518 for the cargo conveyance 504 to be conveyed into and out of the scanning system 500 by the conveyor system 508.

The X-ray source 502 may be positioned so that the lower portion of the X-ray radiation beam is parallel or nearly parallel to the top of the conveyor system 508. If the radiation beam R intercepts the conveyor system 508 and the conveyor system 508 comprises a belt or track, a material that causes low attenuation of radiation may be used. If the conveyor system 508 comprises rollers, a gap may be provided among the plurality of rollers, where necessary. A window may also be provided in the structure supporting the conveyor system 508, if necessary. Collimators (not shown) may be provided between the cargo conveyance 504 and the detector 506 to block scattered radiation from reaching the detector 506. The conveyor system 508 may be reversed to examine a portion or the entire cargo conveyance 504 again or to irradiate the cargo conveyance 504 with a different energy distribution, for example. The cargo conveyance 504 may also be irradiated with multiple energies by rapidly cycling between two or more energy levels as the cargo conveyance 504 is being conveyed through the scanning unit 500.

The detector 506 is electrically coupled to an image processor block 520, which is coupled to a display 522. The image processor block 520 comprises analog-to-digital conversion and digital processing components, as is known in the art. One or more computers 524 is electrically coupled to and controls the operation of one or more of the X-ray source 500, the detector 506, the conveyor system 508, the image processor 520, and the display 522. The connections between the computer and all the components are not shown, to simplify the Figure. The one or more computers 524 may provide the processing functions of the image processor 520, as well.

As shown in FIG. 8, the collimating slot 503a and the X-ray radiation beam R are directed towards the region above the conveyor system 202, to irradiate the cargo conveyance 504. The radiation beam R may diverge over an angle θ. The X-ray source 502 is preferably displaced a sufficient distance from the cargo conveyance 504 so that the beam R intercepts the entire cargo conveyance 504. The angle θ may range from about 30 degrees to about 90 degrees, for example.

The configuration of the detector 506 may depend on the shape of a collimated radiation beam. For example, if the collimated radiation beam R is a fan beam, a one-dimensional detector array 504 comprising a single row of detector elements may be provided. If the collimated radiation beam R is a cone beam, the detector array may comprise a two dimensional detector array 506 comprising two or more adjacent rows of detector elements. The detector array 506 may comprise a plurality of modules of detectors, each comprising one or more rows of detector elements supported in a housing.

The embodiments described above may also be useful in detecting test materials known to emit neutrons under certain test conditions. For example, the material may undergo photoneutron processes, such as the emission of delayed neutrons. The significantly reduced (or eliminated) neutron generation of this embodiment assists identification and classification of test materials by enabling more accurate determination of the number of neutrons emitted by the test materials.

Radiation sources with the low-neutron shielding of the present invention may operate at a single or multiple energy levels. Linear accelerators that may be used to emit radiation at multiple energy levels are described in U.S. Pat. No. 6,366,021 B1, U.S. Pat. No. 4,400,650 and U.S. Pat. No. 4,382,208, which are assigned to the assignee of the present invention and are incorporated by reference, herein. Another linear accelerator that may be used is described in U.S. application Ser. No. 10/745,947, filed on Dec. 24, 2003, which is also assigned to the assignee of the present invention and is incorporated by reference, herein. A Linatron M9 linear accelerator, manufactured by Varian Medical Systems, Inc. of Palo Alto, Calif., may also be used at single or multiple energies.

While cargo conveyances are described above, embodiments of the invention may be used to examine other objects, such as luggage, bags, boxes, etc. In addition, the object may be a patient undergoing radiation scanning or radiation therapy.

While the charged particles discussed above are electrons and the generated radiation is X-ray radiation, other charged particles, such as protons and deuterons, may be used to generate other types of radiation. For example, gamma ray radiation may be generated by the impact of protons on materials such as lithium, carbon, or sulfur.

While the source described above is a linear accelerator, other types of sources may also be used, such as a betatron, cyclotron, or radio frequency quadropole, for example.

The embodiments described herein are examples of implementations of the invention. Modifications may be made to these examples without departing from the scope of the invention, which is defined by the claims, below.

I claim:

1. A radiation source comprising:
a housing;
an acceleration chamber within the housing, the acceleration chamber having a peak acceleration energy greater than the neutron production threshold of tantalum, during use;
a source of charged particles supported by the housing to emit charged particles into the acceleration chamber; and
a target supported by the housing downstream of the acceleration chamber;
wherein:
impact of the target by the accelerated charged particles generates radiation; and
the target consists essentially of at least one isotope having a neutron production threshold greater than the peak acceleration energy.

2. The radiation source of claim 1, wherein:
the peak acceleration energy is less than or equal to 8 MeV; and
the target is chosen from the group consisting of at least one isotope of carbon, aluminum, scandium, titanium, vanadium, manganese, cobalt, and copper.

3. The radiation source of claim 1, wherein:
the peak acceleration energy is greater than 8 MeV and less than or equal to 9 MeV; and
the target is chosen from the group consisting of at least one isotope of aluminum, scandium, vanadium, manganese, cobalt, and copper.

4. The radiation source of claim 1, wherein:
the peak acceleration energy is greater than 9 MeV and less than or equal to 10 MeV; and
the target is chosen from the group consisting of at least one isotope of aluminum, scandium, manganese, and cobalt.

5. The radiation source of claim 1, wherein:
the peak acceleration energy is greater than 10 MeV and less than 11 MeV; and
the target is chosen from the group consisting of at least one isotope of scandium and aluminum.

6. The radiation source of claim 1, wherein:
the peak acceleration energy is greater than 11 and less than about 13.1 MeV; and
the target consists essentially of aluminum.

7. The radiation source of claim 1, further comprising:
a collimator coupled to the housing, the collimator comprising at least one isotope having a neutron production threshold greater than the peak acceleration energy.

8. The radiation source of claim 7, further comprising:
target shielding surrounding at least a portion of the target, the target shielding comprising at least one isotope having a neutron production threshold greater than the peak acceleration energy.

9. The radiation source of claim 1, further comprising:
housing shielding to shield the housing, the housing shielding comprising at least one isotope having a neutron production threshold greater than the peak acceleration energy.

10. The radiation source of claim 1, wherein:
the target consists essentially of at least one isotope of copper.

11. The radiation source of claim 1, wherein the peak acceleration energy is at least about 7.7 MeV.

12. A radiation source comprising:
a housing;
an acceleration chamber within the housing, the acceleration chamber having a peak acceleration energy greater than the lowest neutron production threshold of tungsten, during use;
a source of charged particles supported by the housing to emit charged particles into the acceleration chamber;
a target supported by the housing downstream of the acceleration chamber; and
a collimator coupled to the housing, proximate the target material;
wherein:
impact of the target by the accelerated charged particles generates radiation; and
the collimator comprises at least one isotope having a neutron production threshold greater than the peak acceleration energy.

13. The radiation source of claim 12, wherein the collimator comprises:
at least one first section consisting essentially of at least one isotope having a neutron production threshold greater than the peak acceleration energy; and
at least one second section comprising at least one isotope having a neutron production threshold less than the peak acceleration energy.

14. The radiation source of claim 13, wherein:
the first section is at least partially between the target and the second section.

15. The radiation source of claim 12, further comprising:
target shielding to shield the target, the target shielding material comprising at least one isotope having a neutron production threshold greater than the peak acceleration energy.

16. The radiation source of claim 12, further comprising:
housing shielding to shield the housing, the housing shielding comprising at least one isotope having a neutron production threshold greater than the peak acceleration energy.

17. The radiation source of claim 12, wherein:
the collimator comprises copper.
18. The radiation source of claim 12, wherein:
the peak acceleration energy is greater than the lowest neutron production threshold of molybdenum.
19. The radiation source of claim 18, wherein:
the peak acceleration energy greater than the neutron production threshold of tantalum.
20. A radiation source comprising:
a housing comprising housing material;
an acceleration chamber within the housing, the acceleration chamber having a peak acceleration energy during use;
a source of charged particles supported by the housing to emit charged particles into the acceleration chamber;
a target supported by the housing downstream of the acceleration chamber; and
target shielding surrounding at least a portion of the target; wherein:
impact of the target material by the accelerated charged particles generates radiation; and
the target shielding material comprises:
at least one first section consisting essentially of at least one isotope having a neutron production threshold greater than the peak acceleration energy, proximate the target; and
at least one second section comprising at least one isotope having a neutron production threshold less than the peak acceleration energy;
wherein the at least one first section is at least partially between the target and the at least one second section.
21. The radiation source of claim 20, wherein:
the first section of the target shielding comprises copper.
22. The radiation source of claim 20, wherein the peak acceleration energy is greater than the lowest neutron production threshold of molybdenum.
23. The radiation source of claim 22, wherein the peak acceleration energy is greater than the lowest neutron production threshold of tantalum.
24. The radiation source of claim 20, further comprising:
housing shielding separate from the target shielding, surrounding, at least in part, the housing.
25. The radiation source of claim 20, wherein the peak acceleration energy is greater than the lowest neutron production threshold of tungsten, during use.
26. A radiation source comprising:
a housing;
an accelerator chamber within the housing, the acceleration chamber having a peak acceleration energy of less than a lowest neutron production threshold of copper;
a source of charged particles to emit charged particles into the accelerator chamber;
a target supported by the housing, downstream of the accelerator chamber, wherein impact of the target by the accelerated charged particles generates radiation;
a collimator coupled to the housing, proximate the target;
target shielding at least partially surrounding the target to shield the target;
wherein:
the target, the collimator, and the target shielding comprise copper.
27. The radiation source of claim 26, wherein the collimator comprises:
a first section consisting essentially of copper, proximate the target; and
a second section comprising at least one isotope having a neutron production threshold less than the peak acceleration energy, downstream of the first section.
28. The radiation source of claim 27, wherein the target shielding comprises:
a first section consisting essentially of copper, proximate the target; and
a second section comprising at least one isotope having a neutron production threshold less than the peak acceleration energy
wherein the at least one first section is at least partially between the target and the at least one second section.
29. The radiation source of claim 27, further comprising:
housing shielding to shield the housing;
wherein the housing shielding comprises copper.
30. The radiation source of claim 27, further comprising:
lead shielding surrounding at least a portion of the collimator and the target shielding.
31. The radiation source of claim 27, wherein the peak acceleration energy is less than or equal to about 9 MeV.
32. The radiation source of claim 26, wherein:
the acceleration chamber has a peak acceleration energy greater than the lowest neutron production threshold of tungsten.
33. The radiation source of claim 32, wherein the acceleration chamber has a peak acceleration energy greater than the lowest neutron production threshold of molybdenum.
34. The radiation source of claim 33, wherein the acceleration chamber has a peak acceleration energy greater than the neutron production threshold of tantalum.
35. A method of generating radiation, comprising:
accelerating charged particles to a peak acceleration energy greater than the neutron production threshold of tantalum;
colliding the charged particles with a target consisting essentially of at least one isotope having a neutron production threshold greater than the peak acceleration energy; and
generating radiation from the collision of the charged particles with the target, without generating neutrons.
36. The method of claim 35, further comprising:
collimating the generated radiation by a collimator comprising at least one isotope having a neutron production threshold greater than the peak acceleration energy.
37. The method of claim 35, further comprising:
shielding the target with shielding comprising at least one isotope having a neutron production threshold greater than the peak acceleration energy.
38. The method of claim 35, further comprising:
shielding the housing with shielding material comprising at least one isotope having a neutron production threshold greater than the peak acceleration energy.
39. A system for examining a cargo conveyance, comprising:
a radiation source positioned to irradiate an object; and
a detector positioned to receive radiation after interacting with the object;
wherein the radiation source comprises:
a housing;
an acceleration chamber supported by the housing, the acceleration chamber having a peak acceleration energy of less than the lowest neutron production threshold of copper and greater than the lowest neutron production threshold of tungsten;
a source of charged particles supported by the housing to emit charged particles into the acceleration chamber;

a target supported by the housing downstream of the acceleration chamber;
wherein:
the target consists essentially of at least one isotope of copper; and
impact of the target material by the accelerated charged particles generates radiation, without producing neutrons.

40. The system of claim 39, further comprising:
a collimator coupled to the housing; and
target shielding supported by the housing, partially around the target; and
wherein:
at least one of the collimator and the target shielding comprises copper.

41. The system of claim 39, further comprising:
shielding over at least a portion of the housing;
wherein the shielding comprises copper.

42. The system of claim 39, further comprising:
a conveyor to support the object for scanning and to convey the object through the system, the conveyor being configured to support and convey a cargo conveyance.

43. The system of claim 42, wherein the cargo conveyance has a thickness of at least 5 feet (1.5 meters).

44. The system of claim 43, wherein:
the cargo conveyance is a standard cargo conveyance.

45. The system of claim 39, wherein:
the peak acceleration energy is greater than the lowest neutron production threshold of molybdenum.

46. The system of claim 45, wherein:
the peak acceleration energy is greater than the lowest neutron production threshold of tantalum.

47. The system of claim 39, wherein:
the peak acceleration energy is less than about 9.9 MeV and greater than about 6.1 MeV.

48. A radiation source, comprising:
a housing;
an acceleration chamber within the housing, the acceleration chamber having a peak acceleration energy greater than the neutron production threshold of tantalum, during use;
a source of charged particles supported by the housing to emit charged particles into the acceleration chamber; and
a target supported by the housing downstream of the acceleration chamber;
wherein:
impact of the target by the accelerated charged particles generates radiation; and
the target consists essentially of a low atomic number material comprising at least one isotope having a neutron production threshold greater than the peak acceleration energy.

49. The radiation source of claim 48, wherein the low atomic number material consists essentially of copper.

50. A radiation source comprising:
a housing;
an acceleration chamber within the housing, the acceleration chamber having a peak acceleration energy greater then the neutron production threshold of tantalum and less than about 13.1 MeV, during use;
a source of charged particles supported by the housing to emit charged particles into the acceleration chamber; and
a target supported by the housing downstream of the acceleration chamber, the target consisting essentially of aluminum;
wherein impact of the target by the accelerated charged particles generates radiation.

51. A radiation source comprising:
a housing;
an acceleration chamber within the housing, the acceleration chamber having a peak acceleration energy of at least 6.1 MeV and less than 9.9 MeV, during use;
a source of charged particles supported by the housing to emit charged particles into the acceleration chamber;
a target supported by the housing downstream of the acceleration chamber, wherein impact of the target by the accelerated charged particles generates radiation; and
a collimator coupled to the housing, proximate the target material, the collimator comprising copper.

52. The radiation source of claim 51 wherein the collimator comprises:
at least one first section consisting essentially of copper; and
at least one second section comprising at least one isotope having a neutron production threshold less than the peak acceleration energy.

53. A radiation source comprising:
a housing comprising housing material;
an acceleration chamber within the housing, the acceleration chamber having a peak acceleration energy of at least 6.1 MeV and less than 9.9 Mev;
a source of charged particles supported by the housing to emit charged particles into the acceleration chamber;
a target supported by the housing downstream of the acceleration chamber, wherein impact of the target material by the accelerated charged particles generates radiation; and
target shielding surrounding at least a portion of the target, the target shielding comprising copper.

54. The radiation source of claim 53, wherein the acceleration chamber has a peak acceleration energy greater than the lowest neutron production threshold of tungsten, during use.

55. The radiation source of claim 53, wherein the target shielding comprises:
at least one first section consisting essentially of copper; and
at least one second section comprising at least one isotope having a neutron production threshold less than the peak acceleration energy;
wherein the at least one first section is at least partially between the target and the at least one second section.

56. A method of generating radiation, comprising:
accelerating charged particles to a peak acceleration energy greater than the neutron production threshold of tungsten;
colliding the charged particles with a target;
generating radiation from the collision of the charged particles with the target; and
collimating the generated radiation by a collimator comprising at least one isotope having a neutron production threshold greater than the peak acceleration energy.

57. The method of claim 56, further comprising:
absorbing radiation generated by the target with target shielding comprising at least one isotope having a neutron production threshold greater than the peak acceleration energy.

58. The method of claim 57, further comprising:
absorbing radiation generated by the target by housing shielding comprising at least one isotope having a neutron production threshold greater than the peak acceleration energy.

59. The method of claim 56, further comprising:
absorbing radiation generated by the target by housing shielding comprising at least one isotope having a neutron production threshold greater than the peak acceleration energy.

60. A method of generating radiation, comprising:
accelerating charged particles to a peak acceleration energy;
colliding the charged particles with a target;
generating radiation from the collision of the charged particles with the target, without generating neutrons; and
absorbing a portion of the generated radiation by housing shielding comprising:
at least one first section of material consisting essentially of at least one isotope having a neutron production threshold greater than the peak acceleration energy, proximate the target; and
at least one second section of material comprising at least one isotope having a neutron production threshold less than the peak acceleration energy;
wherein the at least one first section is at least partially between the target and the at least one second section.

61. The method of claim 60, comprising:
accelerating the charged particles to a peak acceleration energy greater than the neutron production threshold of tungsten.

62. The method of claim 60, comprising:
absorbing at least a portion of the generated radiation by at least one first section comprising copper.

63. The method of claim 60, further comprising:
absorbing at least a portion of the generated radiation by target shielding comprising at least one isotope having a neutron production threshold greater then the peak acceleration energy, the target shielding being proximate to the target.

64. A method of examining contents of an object, comprising:
accelerating charged particles to a peak acceleration energy greater than the neutron production threshold of tantalum;
colliding the charged particles with a target consisting essentially of at least one isotope having a neutron production threshold greater than the peak acceleration energy;
generating radiation from the collision of the charged particles with the target, without generating neutrons;
scanning an object by the generated radiation; and
detecting radiation inteacting with the object.

\* \* \* \* \*